United States Patent
Hands et al.

(10) Patent No.: US 7,847,095 B2
(45) Date of Patent: Dec. 7, 2010

(54) PROCESS FOR 5-[[2(R)-[1(R)-[3,5-BIS(TRIFLUOROMETHYL)PHENYL]ETHOXY]-3(S)-(4-FLUOROPHENYL)-4-MORPHOLINYL]METHYL]-1,2-DIHYDRO-3H-1.,2,4-TRIAZOL-3-ONE

(75) Inventors: David Hands, London (GB); Mark Huffman, Warren, NJ (US); Mahmoud S. Kaba, Somerset, NJ (US); Joseph F. Payack, Somerset, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 490 days.

(21) Appl. No.: 10/511,691

(22) PCT Filed: Apr. 17, 2003

(86) PCT No.: PCT/US03/11956

§ 371 (c)(1),
(2), (4) Date: Oct. 14, 2004

(87) PCT Pub. No.: WO03/089429

PCT Pub. Date: Oct. 30, 2003

(65) Prior Publication Data
US 2005/0215786 A1    Sep. 29, 2005

Related U.S. Application Data

(60) Provisional application No. 60/373,734, filed on Apr. 18, 2002.

(51) Int. Cl.
*C07D 413/00* (2006.01)
*A61K 31/535* (2006.01)
(52) U.S. Cl. .................................. 544/132; 514/236.5
(58) Field of Classification Search ................ 544/132; 514/236.5
See application file for complete search history.

(56) References Cited

U.S. PATENT DOCUMENTS

| 5,637,699 | A  | 6/1997  | Dorn et al.    |
|-----------|----|---------|----------------|
| 5,691,336 | A  | 11/1997 | Dorn et al.    |
| 5,719,147 | A  | 2/1998  | Dorn et al.    |
| 6,096,742 | A  | 8/2000  | Crocker et al. |
| 6,229,010 | B1 | 5/2001  | Crocker et al. |
| 6,297,376 | B1 | 10/2001 | Cottrell et al.|

OTHER PUBLICATIONS

CRC Handbook of Chemistry and Physics 80th Edition, CRC Press, 1999, p. 15-18.*

* cited by examiner

*Primary Examiner*—Sun Jae Y. Loewe
(74) *Attorney, Agent, or Firm*—Nicole M. Beeler; David A. Muthard

(57) ABSTRACT

The present invention is concerned with a novel process for the preparation of the compound 5-[[2(R)-[1(R)-[3,5-bis(trifluoromethyl)phenyl]ethoxy]-3(S)-(4-fluorophenyl)-4-morpholinyl]methyl]-1,2-dihydro-3H-1,2,4 -tria-zol-3-one. This compound is useful as a substance P (neurokinin-1) receptor antagonist. In particular, the compound is useful e.g., in the treatment of psychiatric disorders, inflammatory diseases and emesis.

3 Claims, No Drawings

PROCESS FOR 5-[[2(R)-[1(R)-[3,5-BIS(TRIFLUOROMETHYL)PHENYL]ETHOXY]-3(S)-(4-FLUOROPHENYL)-4-MORPHOLINYL]METHYL]-1,2-DIHYDRO-3H-1.,2,4-TRIAZOL-3-ONE

CROSS REFERENCE TO RELATED APPLICATIONS

This application is a U.S. National Phase application under 35 U.S.C. §371 of PCT Application No. PCT/US03/11956, filed Apr. 17, 2003, which claims priority under 35 U.S.C. §119 from U.S. Application No. 60/373,734, filed Apr. 18, 2002.

BACKGROUND OF THE INVENTION

The present invention relates to processes for the preparation of 5-[[2(R)-[1(R)-[3,5-bis(trifluoromethyl)phenyl]ethoxy]-3(S)-(4-fluorophenyl)-4-morpholinyl]methyl]-1,2-dihydro-3H-1,2,4-triazol-3-one, aprepitant,

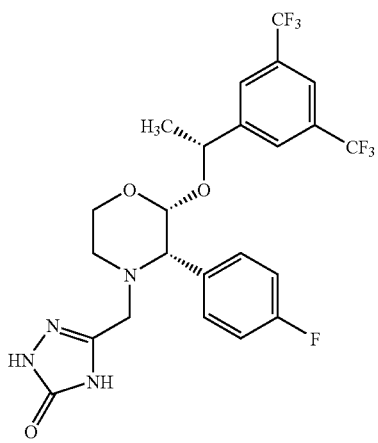

which is a useful therapeutic agent, specifically as a substance P (neurokinin-1) receptor antagonist. This compound is disclosed as having therapeutic utility in U.S. Pat. No. 5,719,147.

U.S. Pat. Nos. 5,637,699, 6,096,742, 6,229,010 and 6,297,376 relate to processes of manufacture and the discovery of polymorphic forms of this compound. In contrast to previously known processes, the present invention provides a more practical and economical method for preparing the compound in relatively high yield and purity. As such, there is a need for a process for the preparation of the compound that is cost-effective and utilizes readily available reagents.

SUMMARY OF THE INVENTION

The present invention relates to a process for preparing a compound of formula 1:

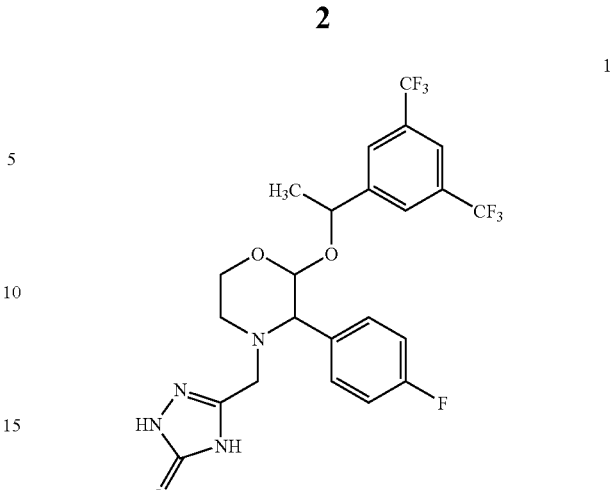

comprising:

cyclizing a compound of formula 4:

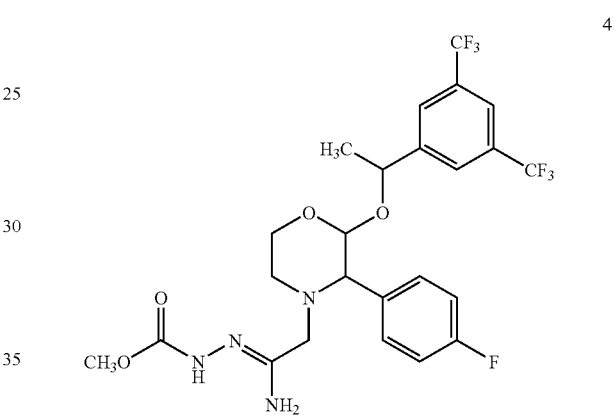

at a temperature of 140-150° C. to produce the compound of formula 1.

In particular, such compounds are substance P (neurokinin-1) receptor antagonists which are useful, e.g., in the treatment of psychiatric disorders, inflammatory diseases and emesis.

DETAILED DESCRIPTION OF THE INVENTION

The present invention relates to a process for preparing a compound of formula 1:

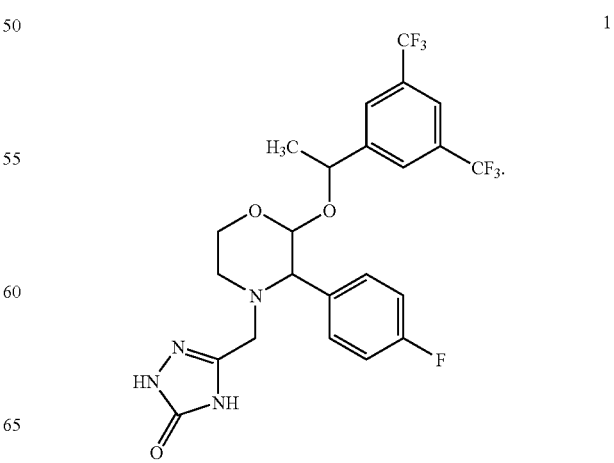

The process comprises:
cyclizing a compound of formula 4:

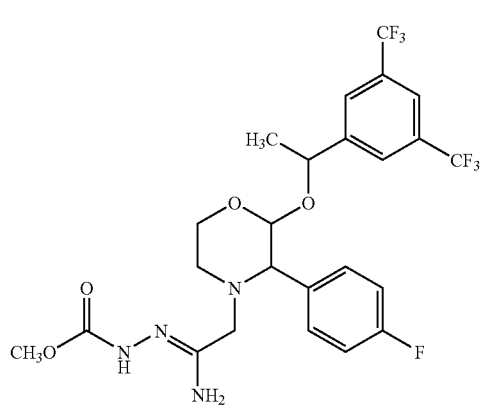

4 at a temperature of 140-150° C. to produce the compound of formula 1.

More particularly, the present invention is directed to processes for the preparation of a compound of formula 1:

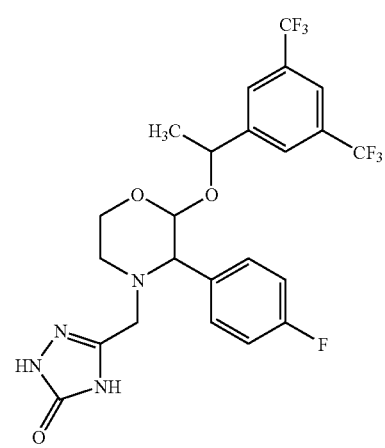

1

The processes are comprised of:
(a) reacting the hydrochloride salt of a compound of formula 2:

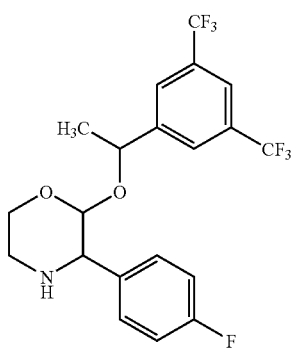

2 in the presence of an inorganic base and toluene with a compound of the formula 3:

Cl—CH₂—C(=NNHCO₂CH₃)—NH₂

3 to produce the compound of formula 4:

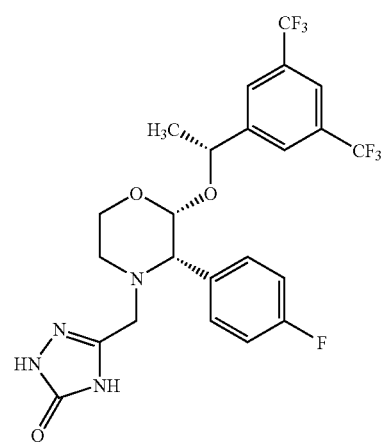

4

(b) washing with an aqueous phase, and
(c) cyclizing at a temperature of 140-150° C. to produce the compound of formula 1.

Even more particularly, a process for preparing a compound of formula

1a is disclosed wherein the hydrochloride salt of a compound of formula 2a:

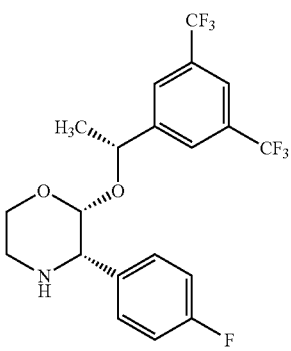

is reacted in the presence of an inorganic base and toluene with a compound of the formula 3:

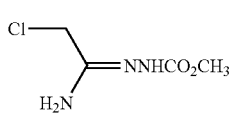

to produce the compound of formula 4a:

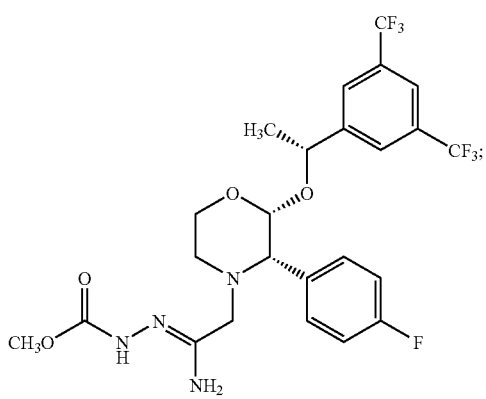

(b) washing with an aqueous phase and
(c) cyclizing at a temperature of 140-150° C. to produce the compound of formula 1a.

The washing step described herein typically uses an aqueous phase, e.g., water, and may optionally contain a salt. Representative examples of salts that are useful herein include KCl, KHCO$_3$, K$_2$CO$_3$, Na$_2$CO$_3$, NaHCO$_3$, NaCl and similar such salts. KCl is the preferred salt.

In another aspect of the invention, the process is further comprised of a drying step prior to cyclization.

As used herein the term "inorganic base" refers to compounds such as sodium carbonate, cesium carbonate, sodium hydroxide, potassium hydroxide, potassium carbonate and the like. More particularly, the preferred inorganic base is potassium carbonate.

More particularly, the present invention relates to the process described above wherein compound 2 or 2a is reacted with compound 3 in the presence of an inorganic base, toluene and a polar aprotic solvent. As used herein, the term "polar aprotic solvent" refers to a solvent that neither donates or accepts protons, and is, for example, selected from the group consisting of: dimethylformamide (DMF), dimethylsulfoxide (DMSO), N-methylpyrrolidone (NMP), acetonitrile (MeCN), N,N-dimethylacetamide (DMAC) and hexamethylphosphoramide HMPA).

The process described herein is surprisingly efficient, minimizing the production of a mixture of isomers, and thus increasing productivity and purity. The subject process also minimizes the use of toxic solvents.

The 2-[1-[3,5-bis(trifluoromethyl)phenyl]ethoxy-3-(4-fluorophenyl)-1,4-oxazine starting material 2 and (2R, 2-alpha-R, 3a)-2-[1-[3,5-bis(trifluoromethyl)-phenyl]ethoxy-3-(4-fluorophenyl)-1,4-oxazine starting material 2a may be obtained in accordance with PCT WO 01/94324 A1 (published Dec. 13, 2001)and US 2002/0052494 A1 (published May 2, 2002), or using modifications thereof. The starting material may be used directly or following purification. Purification procedures include crystallization, distillation, normal phase or reverse phase chromatography. The following example is provided for purposes of illustration and is not intended to limit the disclosed invention.

EXAMPLE 1

[2R-[2α(R*),3α]]-5-[[2-[1-[3,5-bis(trifluoromethyl) phenyl]ethoxy]-3-(4-fluorophenyl)-4-morpholinyl] methyl]-1,2-dihydro-3H-1,2,4-triazol-3-one A mixture of the starting material as the hydrochloride salt of (2R, 2-alpha-R, 3a)-2-[1-[3,5-bis(trifluoromethyl)phenyl] ethoxy-3-(4-fluorophenyl)-1,4-oxazine (2a) (1.00 kg; 2.11 mol) and potassium carbonate (1.02 kg; 7.39 mol) in DMSO (2.2 L) and toluene (1.0 L) was cooled to 15° C. A slurry of amidrazone 3 (367 g; 2.22 mol) in toluene (1.5 L) was added. The mixture was stirred and then partitioned between toluene (4.0 L) and water (5.0 L). The phases were separated at 40° C. The organic layer (containing 4a) was washed with water (5.0 L) at 40° C. and then partially concentrated at atmospheric pressure, providing intermediate 4a, which is used in the next step without isolation. The resulting solution containing intermediate 4a was heated to 140° C. for 3 h and then allowed to cool to RT. The solids were filtered and dried in vacuo at 40° C. The product (1.00 kg) was dissolved in methanol (10.0 L) and 50 g of Darco was added. The mixture was heated at 60° C. for 1 h and then filtered at this temperature. The filtrates were allowed to cool slowly to RT. Water (5.0 L) was added slowly over 1 h. The slurry was cooled to 5° C. and the solids were filtered and dried in vacuo at 40° C. to yield 0.96 kg (85% overall yield) of the product [2R-[2α(R*),3α]]-5-[[2-[1-[3,5-bis(trifluoromethyl)phenyl]-ethoxy]-3-(4-fluorophenyl)-4-morpholinyl]methyl]-1,2-dihydro-3H-1,2,4-triazol-3-one (i.e. 5-[[2(R)-[1(R)-[3,5-bis(trifluoromethyl) phenyl]ethoxy]-3(S)-(4-fluorophenyl)-4-morpholinyl] methyl]-1,2-dihydro-3H-1,2,4-triazol-3-one).

Intermediate 4a: $[\alpha]_D^{25}$ =+84° (c=1.02, methanol); $^1$H NMR (400 MHz, CDCl3) δ 7.64 (s, 2H), 7.34 (br t, J ~7, 2H), 7.16 (s, 1H), 7.03 (t, J=8.4, 2H), 5.8 (very br s, 2H), 4.88 (q, J=6.6, 1H), 4.33 (d, J=2.8, 1H), 4.24 (td, J=11.6, 2.0, 1H), 3.77 (s, 2H), 3.66 (ddd, J=11.6, 3.2, 1.6, 1H), 3.46 (d, J=2.8, 1H), 3.31 (d, J=14.5, 1H), 2.96 (br d, J=11.6, 1H), 2.59 (d, J=14.5, 1H), 2.50 (td, J=12.1, 3.2, 1H), 1.47 (d, J=6.6, 3H). Anal. Calc. for C$_{24}$H$_{25}$F$_7$N$_4$O$_4$: C, 50.89; H, 4.45; F, 23.48; N, 9.89. Found: C, 50.48; H, 4.40; F, 23.43; N, 9.84. Final product 1a: Mp: 255° C.; $[\alpha]_D^{25}$=+69° (c=1.00, methanol); $^1$H NMR (400 MHz, CD$_3$OD) δ 7.70 (s, 1H), 7.51 (m, 2H), 7.32 (s, 2H), 7.04 (t, J=8.7, 2H), 4.94 (q, J=6.3, 1H), 4.35 (d, J=2.8, 1H), 4.28 (td J=11.5, 2.8, 1H), 3.66 (ddd, J=11.5, 3.3, 1.6, 1H), 3.54 (d, J=14.3, 1H), 3.48 (d, J=2.8, 1H), 2.88 (br d, J=11.9, 1H), 2.86 (d, J=14.3, 1H), 2.49 (td, J=11.9, 3.6, 1H), 1.44 (d, J=6.3, 3H); $^{13}$C NMR (100 MHz, CD$_3$OD) δ 164.1 (d, J=245.9), 158.7, 147.6, 147.0, 134.1 (d, J=3.1), 132.7 (d, J=33.4), 132.4 (d, J=8.0), 127.8 (m), 124.6 (q, J=272.0), 122.3 (m), 116.1 (d, J=21.6), 97.1, 73.7, 70.5, 60.4, 53.6, 52.2, 24.7. Anal. Calc. for C$_{23}$H$_{21}$F$_7$N$_4$O$_3$: C, 51.69; H, 3.96;

F, 24.88; N, 10.48. Found: C, 51.50; H, 3.82; F, 24.73; N, 10.44. HRMS: 534.1480 (meas.); 534.1502 (calc. for $C_{23}H_{21}F_7N_4O_3$).

All patents and patent publications cited herein are incorporated by reference in their entirety. While the invention has been described and illustrated with reference to certain particular embodiments thereof, those skilled in the art will appreciate that various adaptations may be made without departing from the spirit and scope of the invention.

What is claimed is:

1. A process for preparing a compound of the formula 1a:

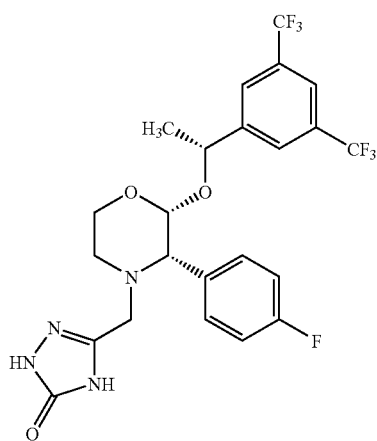

1a comprising:
    reacting the hydrochloride salt of a compound of formula 2a:

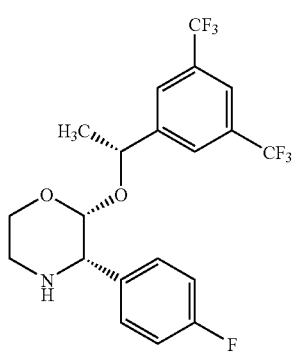

2a in the presence of:
    potassium carbonate;
    toluene; and
    dimethylsulfoxide;
with a compound of the formula 3:

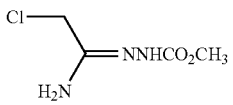

3 to produce a compound of the formula 4a:

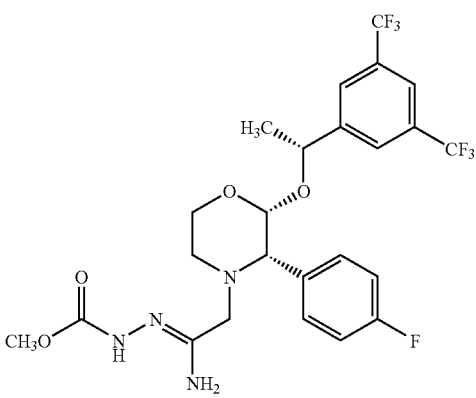

4a washing the compound of formula 4a with an aqueous salt solution;
drying;
and cyclizing the compound of formula 4a at a temperature of 140-150° C. to give the compound of formula 1a.

2. The process of claim 1 wherein the aqueous salt solution contains at least one compound selected from the group consisting of: KCl, KHCO₃, K₂CO₃, Na₂CO₃, NaHCO₃ and NaCl.

3. The process of claim 2 wherein the aqueous salt solution contains KCl.

* * * * *